United States Patent
Lemieux et al.

(10) Patent No.: US 12,194,064 B2
(45) Date of Patent: Jan. 14, 2025

(54) PROCESS OF PRODUCING CONCENTRATED THERAPEUTIC PHOSPHOLIPID COMPOSITION FROM KRILL EXTRACTS CONTAINING HIGH LEVEL OF FREE FATTY ACIDS

(71) Applicant: AKER BIOMARINE HUMAN INGREDIENTS AS, Lysaker (NO)

(72) Inventors: Pierre Lemieux, Laval (CA); Simon Despins, Laval (CA); Sarya Aziz, Laval (CA); Remi Labrecque, Laval (CA)

(73) Assignee: AKER BIOMARINE HUMAN INGREDIENTS AS, Lysaker (NO)

( * ) Notice: Subject to any disclaimer, the term of this patent is extended or adjusted under 35 U.S.C. 154(b) by 572 days.

(21) Appl. No.: 17/427,685

(22) PCT Filed: Feb. 7, 2020

(86) PCT No.: PCT/CA2020/050160
§ 371 (c)(1),
(2) Date: Aug. 2, 2021

(87) PCT Pub. No.: WO2020/163943
PCT Pub. Date: Aug. 20, 2020

(65) Prior Publication Data
US 2022/0125857 A1    Apr. 28, 2022

Related U.S. Application Data

(60) Provisional application No. 62/804,285, filed on Feb. 12, 2019.

(51) Int. Cl.
*C11C 3/06*         (2006.01)
*A61K 31/202*   (2006.01)
(Continued)

(52) U.S. Cl.
CPC .......... *A61K 35/612* (2013.01); *A61K 31/202* (2013.01); *A61K 31/685* (2013.01); *A61K 47/22* (2013.01)

(58) Field of Classification Search
CPC ....................................................... C11C 3/06
See application file for complete search history.

(56) References Cited

FOREIGN PATENT DOCUMENTS

| WO | 2008060163 | 5/2008 |
| WO | 2011050474 | 5/2011 |

(Continued)

OTHER PUBLICATIONS

Castro-Gomez Maria Pilar et al: "Comprehensive Study of the Lipid Classes of Krill Oil by Fractionation and Identification of Triacylglycerols, Diacylglycerols, and Phospholipid Molecular Species by Using UPLC/QToF-MS", Food Analytical Methods, Springer New York LLC, US, vol. 8, No. 10, Mar. 26, 2015 (Mar. 26, 2015), pp. 2568-2580, XP035550595, ISSN: 1936-9751, DOI: 10.1007/S12161-015-0150-6.

(Continued)

*Primary Examiner* — Rosanne Kosson
(74) *Attorney, Agent, or Firm* — Casimir Jones, S.C.; J. Mitchell Jones

(57) ABSTRACT

It is provided processes for generating a therapeutic concentrated phospholipid composition from raw krill oil containing high content of free fatty acids. Particularly it is provided a process producing a concentrated phospholipid composition comprising the steps of: fractionating a raw hill oil (RKO) containing at least 7% of free fatty acids (FFA) obtaining a fraction enriched in phospholipids and an undesired layer; and separating said fraction enriched in phospholipids from the undesired layer, producing the therapeutic concentrated phospholipid composition with a yield of at least 30%.

19 Claims, 2 Drawing Sheets

(51) Int. Cl.
    *A61K 31/685*     (2006.01)
    *A61K 35/612*     (2015.01)
    *A61K 47/22*     (2006.01)

(56) References Cited

FOREIGN PATENT DOCUMENTS

| WO | 2011051743 | 5/2011 |
|---|---|---|
| WO | 2015104401 | 7/2015 |
| WO | 2016075669 | 5/2016 |

OTHER PUBLICATIONS

Araujo Pedro et al: "Determination and Structural Elucidation of Triacylglycerols in Krill Oil by Chromatographic Techniques", Lipids, Springer, DE, vol. 49, No. 2, Nov. 5, 2013 (Nov. 5, 2013), pp. 163-172, XP035365601, ISSN: 0024-4201, DOI: 10.1007/S11745-013-3855-6.

Xie, D. et al.: "Antarctic Krill (*Euphausia superba*) Oil: A Comprehensive Review of Chemical Composition, Extraction Technologies, Health Benefits, and Current Applications", Comprehensive Reviews in Food Science and Food Safety, vol. 18, Feb. 12, 2019 (Feb. 12, 2019), pp. 514-534, XP055732800.

Tian Xiaoqing, Fan Chengqi, Liu Zhidong, Huang Hongliang, Lu Yanan: "An Effective Extract Method of Phospholipids from Antarctic Krill *Euphausea superba*", Open Journal of Marine Science, vol. 8, 2018, pp. 293-299, XP055732803.

Sun, W. et al.: "The comparison of krill oil extracted through ethanol-hexane method and subcritical method", Food Sci. Nutr., vol. 7, No. 2, Jan. 28, 2019 (Jan. 28, 2019), pp. 700-710, XP055732804.

PROCESS OF PRODUCING CONCENTRATED THERAPEUTIC PHOSPHOLIPID COMPOSITION FROM KRILL EXTRACTS CONTAINING HIGH LEVEL OF FREE FATTY ACIDS

CROSS REFERENCE TO RELATED APPLICATIONS

The present application claims benefit of U.S. Provisional Application No. 62/804,285 filed Feb. 12, 2019, the content of which is hereby incorporated by reference in its entirety.

TECHNICAL FIELD

It is provided a method of producing concentrated therapeutic phospholipid composition using raw krill oil with a free fatty acid content of more than 7%.

BACKGROUND

Krill oil compositions have been described as providing beneficial effects in human such as decreasing cholesterol, inhibiting platelet adhesion, inhibiting artery plaque formation, preventing hypertension, controlling arthritis symptoms, enhancing transdermal transport, reducing the symptoms of premenstrual symptoms or controlling blood glucose levels in a patient (WO 02/102394).

It is known that components of the extracted oil from krill will vary depending on the nature of the starting material. The factors that affect the lipid content and profile of krill oil are the season, species and age. Storage and processing conditions of the starting material also have an impact on the oil components. For example, the harvesting technique and the storage manner of the krill is stored prior to processing will influence the amount of certain components in the resulting oil. Pre-processing steps, such as heating, cooling (including freeze-drying), and washing are also factors that influence the final components contained in the extracted oil.

Extraction protocols of krill oil have been described. U.S. patent application no. 2010/0143571 discloses that when preparing a lipid fraction from fresh krill, krill lipases remain active after the krill is dead hydrolyzing part of the krill lipids. According to the U.S. patent application no. 2010/0143571, the hydrolysis of lipids carried out by these lipases is an issue and undesired. In consequence, it is described a process that will provide for a low degree of hydrolysis of the krill lipids thus minimizing the risk of resulting in a krill oil containing an undesired amount of free fatty acids. Accordingly, pre-processing steps when handling of the raw materials is desired, such as, a heat pre-treatment of the krill to inactivate enzymatic decomposition of the lipids, ensuring a product with a low level of free fatty acids (FFA).

U.S. Pat. No. 9,028,877 describes extracts from Antarctic krill having high levels of astaxanthin, phospholipids, including enriched quantities of ether phospholipids, and omega-3 fatty acids. More particularly, U.S. Pat. No. 9,028,877 discloses a method for processing freshly caught krill at the site of capture such as on board of a ship in order to minimize processing of frozen krill that are transported from the capture site to the processing site, which transportation is expensive and may result in the degradation of the krill starting material. The krill is first subjected to a protein denaturation step, such as a heating step, to avoid the formation of enzymatically decomposed oil constituents, such as free fatty acids.

International application no. WO 2011/050474 discloses concentrated therapeutic phospholipid (PL) compositions, comprising for example about 60% w/w phospholipids. These concentrated therapeutic phospholipid compositions are produced using krill oil starting materials as described in U.S. patent application no. 2010/0143571 and U.S. Pat. No. 9,028,877. Such krill oil starting materials do not allow to yield an economically viable commercial amount of these concentrated therapeutic PL compositions for use in the pharmaceutical industry in a consistent manner.

International application no. WO 2019/111055 discloses a method of producing a protein phospholipid complex from a crustacean where hydrolysis occurs without denaturing the protein.

There is thus still a need to be provided with a method for processing krill in order to produce economically viable commercial amount of concentrated therapeutic PL composition in a consistent and efficient way for use in the pharmaceutical industry.

SUMMARY

It is provided a process for producing a concentrated therapeutic phospholipid composition comprising the steps of extracting a raw krill oil (RKO) containing at least 7% of free fatty acids (FFA) obtaining a fraction enriched in phospholipids and an undesired layer; and separating the fraction enriched in phospholipids from the undesired layer.

In an embodiment, the process described herein produces the therapeutic concentrated phospholipid composition with a yield of at least 30%.

In another embodiment, the process described herein produces the therapeutic concentrated phospholipid composition with a yield between 30%-60%.

In a further embodiment, the total phospholipids in the therapeutic concentrated phospholipid composition are at a concentration of at least 50% (w/w (phospholipids/composition)).

In an embodiment, wherein the concentrated therapeutic phospholipid composition comprises free and bounded docosahexaenoic acid (DHA) and eicosapentaenoic acid (EPA), wherein the total free and bound EPA in the composition is at a concentration of between 15% and 25% (w/w), and the total free and bound DHA in the composition is at a concentration of between 10% and 15% (w/w).

In a further embodiment, the concentrated therapeutic phospholipid composition comprises compounds of the Formula I:

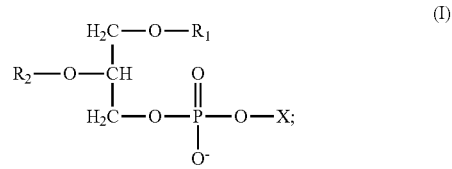

wherein $R_1$ and $R_2$ each independently optionally represent a docosahexaenoic acid (DHA) or an eicosapentaenoic acid (EPA) residue; and wherein each X is independently selected from —$CH_2CH_2NH_3$, —$CH_2CH_2N(CH_3)_3$ and

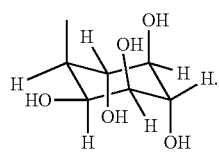

In another embodiment, the RKO comprises at least 7% of FFA.

In an embodiment, the RKO comprises at least 15% of FFA.

In a further embodiment, the RKO is fractioned by countercurrent supercritical $CO_2$ extraction.

In an additional embodiment, the RKO is mixed with solvent to be fractioned into a first low density layer and a first higher density enriched in phospholipids; separating the first higher density enriched in phospholipids from the first low density layer; mixing the first separated higher density enriched in phospholipids with an organic solvent comprising at least about 85% by weight of a C3-C8 ketone solvent to a mixture; fractionating the mixture into a second low density layer and a second layer enriched in phospholipids; separating the second layer enriched in phospholipids from the second low density layer obtaining the concentrated phospholipid composition.

In an embodiment, the process comprises mixing the RKO and a first organic solvent at a ratio of about 5 to about 15 in units of volume organic solvent:kg RKO.

In an embodiment, the concentrated phospholipid composition is mixed with one or more free fatty acids.

In another embodiment, the organic solvent comprises at least about 85% by weight of the a C3-C8 ketone solvent.

In an additional embodiment, the process described herein further comprises combining the second layer enriched in phospholipids with a stabilizing agent, a viscosity-reducing agent, or a combination thereof, to produce a phospholipid-enriched fraction.

In an embodiment, the process comprises fractioning at least 100 kg of RKO.

In an embodiment, it is encompassed prior to mixing the RKO and the first organic solvent, the process comprises heating the RKO to a temperature from about 20° C. to about 70° C.

In a further embodiment, the process described herein further comprises directing the mixture of RKO in solvent through a filter.

In an embodiment, the filter is a 0.45 μm filter.

In an embodiment, the process described herein further comprises directing the mixture RKO in solvent through a first filter and a second filter.

In an embodiment, the first filter is a 10 μm filter and the second filter is a 0.45 μm filter.

In another embodiment, the process described herein further comprises combining the second layer enriched in phospholipids with a viscosity-reducing agent.

In an embodiment, the second layer enriched in phospholipids is combined with the viscosity-reducing agent at a ratio of about 0.1 to about 0.3.

In an embodiment, the stabilizing agent comprises Vitamin E.

In an embodiment, the process is a continuous process.

In a further embodiment, the total phospholipids in the therapeutic phospholipid composition are at a concentration of 55% (w/w (phospholipids/total composition)).

In an embodiment, the total phospholipids in the therapeutic phospholipid composition are at a concentration of 60% (w/w (phospholipids/total composition)).

In another embodiment, the total phospholipids in the therapeutic phospholipid composition are at a concentration of 90% (w/w (phospholipids/total composition)).

In an additional embodiment, the therapeutic phospholipid composition comprises triglycerides in a concentration of below about 5% (w/w).

In an embodiment, the RKO is made from frozen krill or krill meal.

BRIEF DESCRIPTION OF THE DRAWINGS

Reference will now be made to the accompanying drawings.

DETAILED DESCRIPTION

Figure 1:
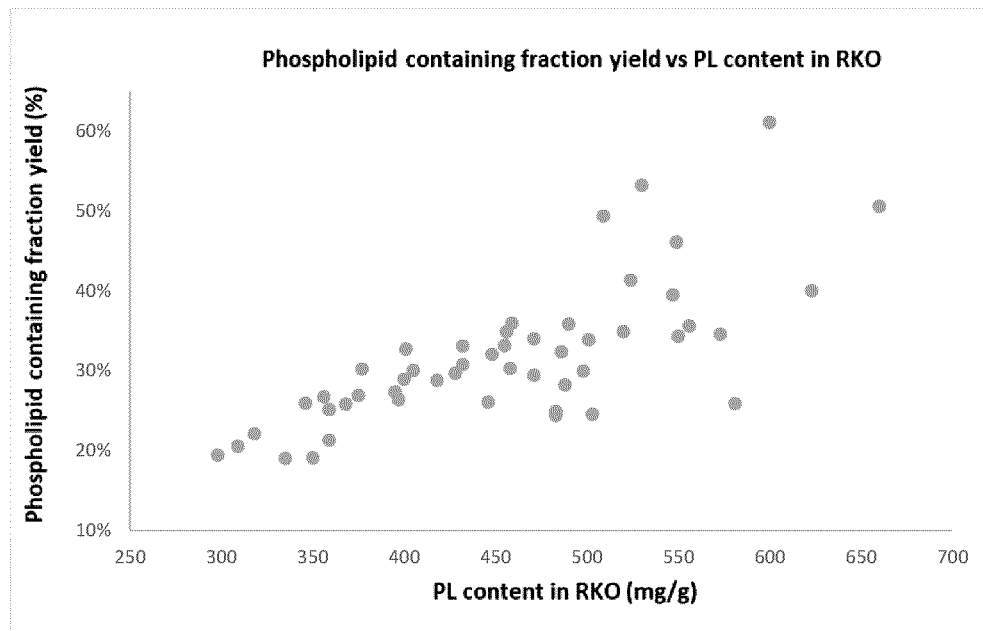
FIG. 1 illustrates the correlation between the PL content in phospholipid containing fraction and PL content in krill oil starting materials.

In accordance with the present description, it is provided a process of extracting an oil from krill wherein the resulting oil contains high content of free fatty acids (FFA).

International application no. WO 2011/050474 discloses concentrated therapeutic phospholipid (PL) compositions, comprising for example about 60% w/w phospholipids, which have surprising effects in the treatment of cardiovascular diseases, notably by reducing triglyceride (TG) levels. These concentrated therapeutic phospholipid compositions are produced from krill oil starting materials as described herein.

The concentrated therapeutic phospholipid composition can be made or produced by any method known in the art. However, the yield of the resulting therapeutic concentrated phospholipid composition will be low, making it not economically viable. Also, this composition is produced using proprietary process which controls the variability of the krill and allow to reach consistently the targeted specifications of the therapeutic product. Therefore, since such composition will be subject to regulatory approval, the manufacturing process will need to be consistent and efficient.

Initially, phospholipid containing oils can be isolated from natural sources which can then be further processed.

Accordingly, in an embodiment, it is provided a process for producing a concentrated phospholipid composition comprising the steps of extracting a raw krill oil (RKO) containing at least 7% of free fatty acids (FFA) obtaining a fraction enriched in phospholipids and an undesired layer; and separating said fraction enriched in phospholipids from the undesired layer, producing the concentrated phospholipid composition.

In an embodiment, said concentrated therapeutic phospholipid composition comprises
compounds of the Formula I:

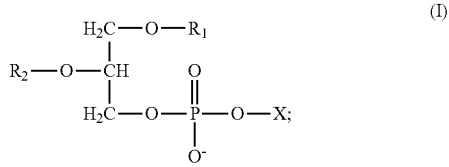

wherein $R_1$ and $R_2$ each independently may or optionally represent a docosahexaenoic acid (DHA) or an eicosapentaenoic acid (EPA) residue; and
wherein each X is independently selected from —$CH_2CH_2NH_3$, —$CH_2CH_2N(CH_3)_3$ and

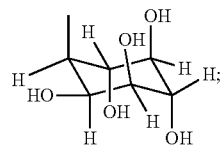

and
free EPA and free DHA, wherein the total free and bound EPA in the composition is at a concentration of between 15% and 25% (w/w), and the total free and bound DHA in the composition is at a concentration of between 10% and 15% (w/w), wherein the total phospholipids in the composition are at a concentration of at least 50% (w/w (phospholipids/composition)).

Harvesting/storage techniques that can be used to increase FFA in the resulting raw krill oil (RKO) include and are not limited to the use of enzymes on freshly caught krill, storing the krill for a specific period of time prior to processing allowing the naturally containing lipases in krill to hydrolyze the lipids levels.

Time and temperature during freezing of krill and addition of enzymes are some of the techniques that can be used to increase the concentration of FFA in Frozen Krill.

In an alternate embodiment, the frozen krill described and encompassed herein can be dried and/or cooked in order to produce krill meal such as to increase the level of FFA.

At this stage, krill meal or frozen krill is stored. The difference in storage temperature and time can influence the level of FFA of the resulting RKO. The actual extraction step can be conducted as described in international application no. WO 2011/050474 (the content of which is incorporated by reference herein in its entirety), wherein frozen krill is mechanically crushed and incubated with a solvent in a ratio of 9:1 acetone water for 60-90 minutes at 8° C. to extract different proportions of the lipids (PL, TG and FFA) from the krill biomass. Lipids are subsequently separated from proteins and krill material by filtration under pressure (50-60 kpa). The solid phase is discarded. The soluble extract is evaporated by a continuous distillation column under vacuum to remove the solvent (acetone). The major part of the aqueous (water) fraction is separated from the lipid fraction by decantation and the remaining water removed by evaporation under vacuum and gentle heating. Those fractions are dosed, analyzed, and blended to constitute an intermediary krill oil product which is re-analyzed to achieve desired specifications and resulting in a krill oil starting material or RKO. Enzymes can be added to increase the level of FFA concentration in the RKO.

It is thus encompassed in an embodiment the use of an RKO with a FFA content of more than 7%, preferably of 8%, more preferably of 15% to produce a concentrated phospholipid composition.

Subsequently, the bulk RKO is further processed in order to produce a concentrated therapeutic phospholipid composition. This krill oil starting material can be further processed using countercurrent supercritical $CO_2$ extraction to concentrate the compositions to produce a concentrated therapeutic phospholipid composition. For example, countercurrent supercritical $CO_2$ extraction at 70° C. and 30 MPa can be used to remove certain biomolecules such as all triglycerides from the krill oil starting material. As more of the TGs are removed from the bulk krill oil starting material, the concentration of the phospholipids increases. When the TGs have been removed through this process the phospholipid composition is at about 60-66% concentration (w/w (phospholipids/composition)). Encompassed herein is a process of producing a concentrated therapeutic phospholipid composition having a phospholipid concentration up to about 90% (w/w (phospholipids/composition)).

Alternatively, as described in WO2019/218062, the content of which is incorporated by reference herein in its entirety, the RKO is fractioned in a vessel already containing acetone under agitation. The RKO/acetone mixture is pumped to a container through a solvent-resistant filtration train including pre-filters of 10 μm porosity and a final filter with a porosity of 0.45 μm to provide a filtered mixture of RKO/acetone. To the filtered mixture of RKO/acetone is added to water under constant agitation. The mixture is then allowed to settle in the process vessel until an upper light phase (i.e., a low density layer) and a lower heavy phase (i.e., a high density layer) are observed where the light phase is clear and a clean interphase is observed between the light and heavy phases. Upon reaching this stage, the heavy phase is transferred into another vessel and the volume calculated. Half the volume of the heavy phase was then added under constant agitation to a vessel, followed by addition of acetone, and subsequently transferring the remaining half of the heavy phase to the same vessel. Agitation is continued and the resulting mixture allowed to settle in the process vessel until two phases are present (a low density light phase and a high density heavy phase), where the light phase is clear and a clean interphase is observed between the light and heavy phases. Upon achieving such settling, the heavy phase (which contains the refined phospholipids) is then transferred into a container. Absolute ethanol is added as a viscosity lowering agent in the vessel under constant agitation. Vitamin E preparation (α-tocopherol) is added to the heavy phase as an antioxidant. The mixture is then agitated to provide a phospholipid-enriched fraction. The total duration for the batch process from RKO to phospholipid-enriched fraction is about 24 hours or less, but can be increased if desired to provide for longer durations for phase separation and/or to account for larger-sized vessels.

Thus, in an embodiment, it is encompassed that the RKO is fractioned into a first low density layer and a first higher density enriched in phospholipids; separating the first higher density enriched in phospholipids from the first low density layer; mixing the first separated higher density enriched in phospholipids with an organic solvent comprising at least about 85% by weight of the a C3-C8 ketone solvent to a mixture; fractionating the mixture into a second low density layer and a second layer enriched in phospholipids; separating the second layer enriched in phospholipids from the second low density layer obtaining the concentrated phospholipid composition. In an embodiment, the organic solvent comprises at least about 85% by weight of the a C3-C8 ketone solvent and an aqueous portion. Alternatively, the second layer enriched in phospholipids can be combined with a stabilizing agent, a viscosity-reducing agent, or a combination thereof, to produce a phospholipid-enriched fraction. For example, the process comprises fractioning at least 100 kg of RKO as starting material. The RKO can be mixed with a first organic solvent at a ratio of about 5 to about 15 in units of volume organic solvent:kg RKO.

Accordingly, when the RKO material comprises a FFA content of more than 7% (see Table 1), the yield of further processing to obtain a final desired concentrated therapeutic phospholipid composition is of at least 30%, preferably between 30-60%. When using a krill oil starting material comprising 6.9% of FFA (see starting material #6, Table 1), the yield of the final concentrated therapeutic phospholipid composition was of 48.8%, compared to 50.8% or 54.1% when krill oil starting material comprising 8% or 8.4% of FFA (see starting material #5 or 6 respectively, Table 1).

TABLE 1

| Starting material krill oil | Sample | Targeted specifications | Starting material krill oil | | | | | | | | | |
|---|---|---|---|---|---|---|---|---|---|---|---|---|
| | | | 1 | 2 | 3 | 4 | 5 | 6 | 7 | 8 | 9 | 10 |
| | Total PL (mg/g) | >25% w/w | 39.5 | 45.8 | 41.8 | 62.3 | 57.3 | 52.4 | 48.8 | 58.1 | 35.6 | 54.7 |
| | Total EPA (mg/g) | >10% w/w | 14.9 | 13.0 | 12.4 | 17.3 | 15.8 | 15.1 | 11.8 | 12.1 | 11.8 | 16.7 |
| | Total DHA (mg/g) | >5% w/w | 9.1 | 7.1 | 6.5 | 8.8 | 10.6 | 10.3 | 16.8 | 6.1 | 6.5 | 8.2 |
| | FFA (%) | >7% w/w | N/Ap | 6.0 | 4.8 | 8.4 | 8.0 | 6.9 | 3.2 | 2.6 | 6.5 | 5.5 |
| | TG (%) | N/Ap | N/Ap | 31.6 | 8.4 | 13.6 | 19.7 | 26.2 | 31.7 | 27.0 | 42.7 | 23.5 |
| Phospholipid containing fraction | Yield (%) | N/Ap | 27.34% | 30.29% | 28.80% | 40.00% | 34.57% | 41.35% | 28.23% | 25.89% | 26.73% | 39.50% |
| Free fatty acid containing fraction | Yield (%) | N/Ap | 24.75% | 14.83% | 15.21% | 20.79% | 19.05% | 17.08% | 12.83% | 9.68% | 12.48% | 13.18% |
| Concentrated therapeutic PL | Total PL (mg/g) | >60% w/w | 63.3 | 62.1 | 63.3 | 80.7 | 81.1 | 71.1 | 60.3 | 60.2 | 60.2 | 67.9 |
| | Total EPA (mg/g) | 15-25% w/w | 19.2 | 19.5 | 20.2 | 21.1 | 18.6 | 18.5 | 16.3 | 16.0 | 18.8 | 20.4 |
| | Total DHA (mg/g) | 10-15% w/w | 11.9 | 11.0 | 10.7 | 10.7 | 12.5 | 12.6 | 9.99 | 8.5 | 10.6 | 10.4 |
| | Yield (%) | N/Ap | 42.1% | 18.5% | 18.3% | 54.1% | 50.8% | 48.8% | 24.3% | 15.4% | 15.6% | 24.0% |

Additionally, in an embodiment, also encompassed is heating the RKO to a temperature from about 20° C. to about 70° C. Also encompassed is the combining of the second layer enriched in phospholipids with a viscosity-reducing agent. In an embodiment, the stabilizing agent comprises Vitamin E.

The process can be continuous as follows. Preheated RKO (between 30° C. and 65° C.) and acetone are fed using calibrated pumps where mixing of RKO and acetone is performed using a mixing pump. The resulting RKO/acetone mixture is filtered in-line through a 10 μm and 0.45 μm pore size filter. The filtered RKO/acetone feed is directed to a static mixer along with a softened water feed, where each feed utilized calibrated pumps to ensure a flow rate of water and a flow rate for the filtered RKO/acetone feed. The static mixer inputs to a horizontal settler, where a light phase and a heavy phase (containing phospholipids) are each continuously collected at the settler extremity. The horizontal settler is maintained at a temperature from 20-25° C.

The heavy phase could then be directed to a second static mixer, to which a concurrent feed of acetone is also directed. From the static mixer a resulting mixture flows to a vertical settler maintained at a temperature of 20-25° C., where the vertical settler provides a light phase and a heavy phospholipid-containing phase. Each phase is continually withdrawn from the vertical settler.

For storage, the phospholipid-enriched fraction is transferred to a container under a blanket of nitrogen, hermetically sealed, and stored at 2-8° C.

As seen in FIG. 1, there is a strong correlation between the phospholipid (PL) containing fraction yields and the PL content in krill oil starting materials (RKO). The yield increases with an increase in PL content.

Figure 2:
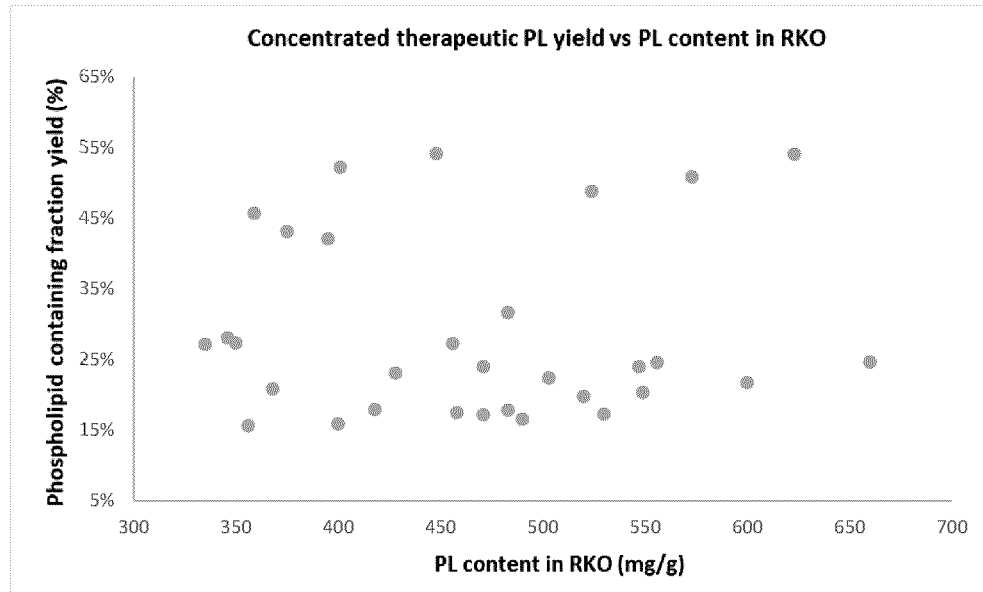
FIG. 2 illustrates the correlation between the final concentrated therapeutic phospholipid composition yields and the PL content in the krill oil starting material extracts.

On the contrary, no correlation was observed between the concentrated therapeutic phospholipid composition yields and PL content in RKO in the evaluated range of PL (FIG. 2).

Figure 3:
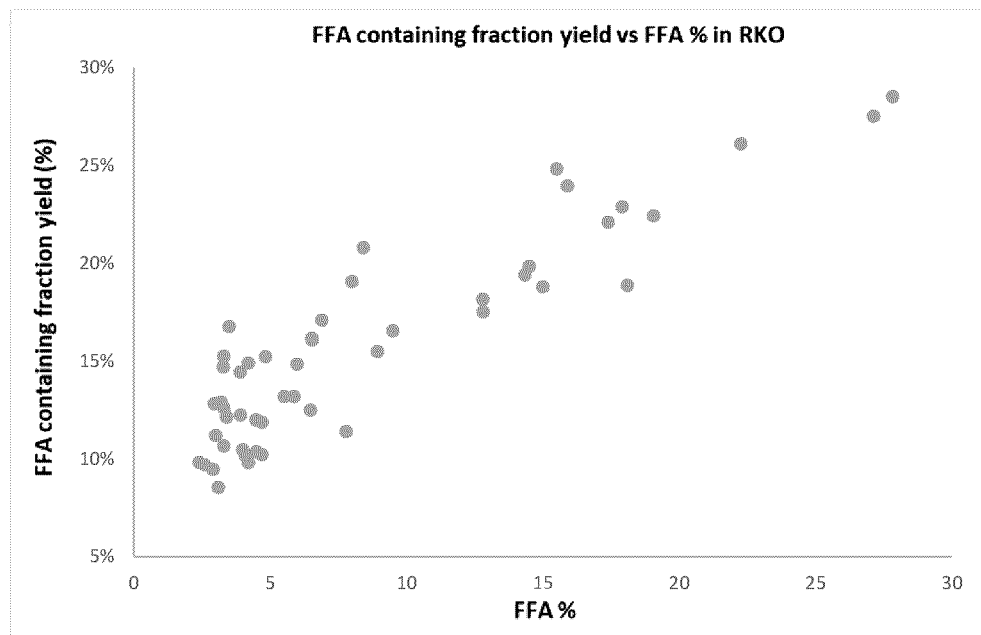
FIG. 3 illustrates the correlation between free fatty acid containing fraction yield and the level of free fatty acid in percentage (FFA %) in krill oil starting materials.

On the other hand, there is a strong correlation between the yield of FFA containing fraction yields and the FFA level in percentage (FFA %) in RKO. All parameters increase along with an increased FFA % content of the krill oil starting material (FIG. 3).

Figure 4:
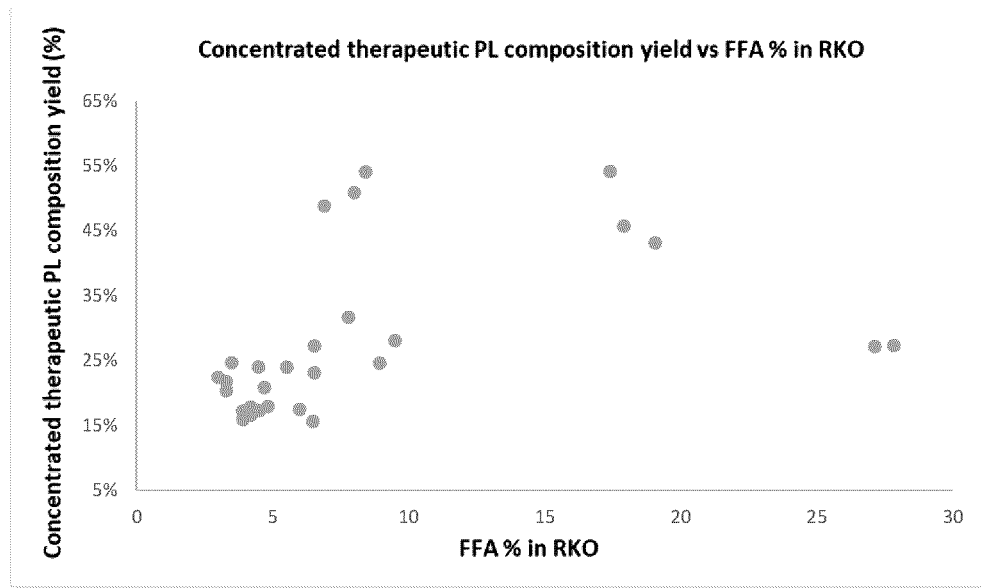
FIG. 4 illustrates the correlation between the final concentrated therapeutic phospholipid composition yields and the level of free fatty acid percentage (FFA %) in krill oil starting materials.

Within the tested range of FFA %, there is a slight correlation between the concentrated therapeutic PL composition yields and FFA % (FIG. 4).

Accordingly, in order to obtain an efficient yield of extraction of concentrated therapeutic phospholipid composition, the minimum threshold to begin obtaining a free fatty acid containing fractions with satisfactory yields and within specification are at around 7-8% FFA and more. Ideally, the level of FFA in the starting material is desired to be around 15%.

It is thus encompassed in an embodiment the use of an RKO with a FFA content of more than 7%, preferably of 8%, more preferably of 15% to produce a concentrated phospholipid composition. In an embodiment, the total phospholipids in the concentrated phospholipid composition are at a concentration of 50% (w/w (phospholipids/total composition)), preferably at a concentration of 55% (w/w (phospholipids/total composition)), more preferably, at a concentration of 60% (w/w (phospholipids/total composition)). In in embodiment, the concentrated phospholipid composition comprises triglycerides in a concentration of below about 5% (w/w).

Example I

Production of RKO with High Level of Free Fatty Acids from Frozen Krill

Fresh krill is harvested using pumps or trawl nets, brought onto the fishing boat and stored in collection wells. Krill is further washed and then drained of its excess water, placed in molds and frozen on board into frozen krill blocks. Frozen krill blocks are packaged and stored on board. Frozen krill is sent to shore where it is kept frozen in storage until used later in the extraction process.

Oil is extracted from frozen krill by crushing whole blocks and transferring the crushed krill in a tank where acetone is added and put under agitation. The mixture is left under constant agitation for about 60 minutes and then is sent through a filter to separate the krill residue from the acetone solution containing the extracted oil. The filtrate is sent to a distillation column to remove and purify the acetone from the solution.

The resulting mixture is comprised of water and the extracted krill oil. The mixture is sent in a settler where the krill oil will float on top of the water phase. Oil is collected by overflow and transferred in an evaporator where residual acetone and water is removed. Dried krill oil is sent in storage tanks and further packaged in drums and put in storage. Oil produced will further be used as RKO in the preparation of concentrated phospholipid composition as described in Example II.

Example II

Production of RKO with High Levels of Free Fatty Acids from Krill Meal and Further Processing into Concentrated Therapeutic Phospholipid Composition Fresh krill is harvested using pumps or trawl nets, brought onto the fishing boat and stored in collection wells. Krill is further washed and then drained of its excess water, placed in molds and frozen on board into frozen krill blocks. Frozen krill blocks are packaged and stored on board. Frozen krill is sent to shore where it is kept frozen in storage until used later in the process.

Frozen krill blocks are crushed and pumped into a cooker where the crushed krill is boiled at 90 to 95° C. Boiled krill is transferred in a decanter centrifuge to remove the excess water. The solid phase obtained is sent to a dryer where the moisture of the solid phase will be reduced to 5-15%, the dried solids is chilled to a temperature below 35° C. and milled to reduce its particle size and transported to a bagging silo to be packaged, sealed in bags and stored at temperatures below −18° C. until used later in the extraction process.

Oil is extracted by transferring the krill meal in an extraction tank where 95% ethanol is added and put under agitation. The mixture is left under constant agitation for about 60 minutes and then is sent through a filter to separate the krill residue from the ethanol solution containing the extracted oil.

The solution obtained is sent to an evaporator where the ethanol is removed. Anhydrous ethanol is then added to the oil to remove proteins, salts and impurities and filtered through a 0.5 μm filter. Filtrate is sent to an evaporator where it is evaporated to dryness under vacuum. The dried oil goes through a sterilization process where it is heated at 70° C. for 30 minutes.

Krill oil is further diluted with 3 L of 95% ethanol per kg of oil. The mixture is incubated for 2 h at −20° C. Following the incubation, the mixture is brought back to room temperature where two layers are formed, an upper layer concentrated in phospholipids and a lower layer concentrated in triglycerides.

The upper layer is collected and fed to a horizontal thin film evaporator. The mixture is pushed against the heated wall (105° C.) of the evaporation chamber and a counter current nitrogen flow increases the drying efficiency. Near the desired concentrated composition outlet, the composition substance temperature (NMT 100° C.) is recorded to ensure a stable drying performance of the equipment.

Dried concentrated composition is recovered in a mold, cooled, unmolded and cut in a portion of about 1 Kg. The pieces are wrapped in LDPE bag and wrapped in Mylar bag are sealed and place in fiber drum. Once labeled, the drums are stored in a cold room at 2-8° C. as QC for testing.

Example III

Production of RKO with High Levels of Free Fatty Acids with Enzymatic Treatment and Further Processing into Concentrated Therapeutic Phospholipid Composition Fresh krill is harvested using pumps or trawl nets, brought onto the fishing boat and stored in collection wells. Krill is further washed and then drained of its excess water and sent to a feed tank.

From the feed tank, krill is pumped into a cooker where the krill is boiled at 90 to 95° C. Boiled krill is transferred in a decanter centrifuge to remove the excess water. The solid phased obtained is sent to a dryer where the moisture of the solid phase will be reduced to 5-15%. The dried solids is chilled to a temperature below 35° C. and milled to reduce its particle size and transported to a bagging silo to be packaged, sealed in bags and stored at room temperature on board. Bags of krill meal are transported to shore where it is stored at temperatures below −18° C. until used later in the extraction process.

Oil is extracted by transferring the krill meal in an extraction tank where 95% ethanol is added and put under agitation. The mixture is left under constant agitation for about 60 minutes and then is sent through a filter to separate the krill residue from the ethanol solution containing the extracted oil.

The solution obtained is sent to an evaporator where the ethanol is removed. Anhydrous ethanol is then added to the oil to remove proteins, salts and impurities and filtered through a 0.5 μm filter. Filtrate is sent to an evaporator where it is evaporated to dryness under vacuum.

Lipolytic enzymes and water is added to the oil to perform controlled enzymatic hydrolysis of the oil in order to generate free fatty acids. Following the reaction, the oil is heated in order to deactivate the enzymes and stop the enzymatic reaction. The oil is further sent in an evaporator where it is evaporated to dryness under vacuum. Krill oil is then packaged and put in storage.

Krill oil is charged into a supercritical $CO_2$ extraction system. $CO_2$ is introduced to the system. Once the conditions in the extractor have reached the specified operating temperature and pressure, the flow of supercritical $CO_2$ is passed through the oil. The heated and pressurized supercritical $CO_2$ extracts triglyceride concentrated oil and concentrates the phospholipids remaining in the extraction vessel. The supercritical $CO_2$ and the extracted triglyceride concentrated oil enters the separator, which is operated at a pressure and temperature sufficient to flash the $CO_2$ (900 psi and 45° C.), causing the extracted triglyceride concentrated oil fraction to precipitate from the gas. The contents of the separator are drained periodically and weighed. The gas continues on a recycle loop through the extractor vessel until the process reaches an established and calculated extent of extraction end-point.

Once the extent of extraction end point is reached, the phospholipids concentrated material remaining in the extractor is drained directly into pre-weighed pails. The amount of product collected is weighed, an analytical sample is taken, and the pail is labeled. The pails are stored in a cold room at 2-8° C. as QC for testing.

What is claimed is:

1. A process for producing a therapeutic concentrated phospholipid composition comprising the steps of:
   harvesting fresh krill in absence of any denaturation step and extracting a raw krill oil (RKO) containing at least 7% of free fatty acids (FFA);
   fractionating said RKO containing at least 7% of FFA to obtain a fraction concentrated in phospholipids and an undesired layer; and
   separating said fraction concentrated in phospholipids from the undesired layer, wherein the therapeutic concentrated phospholipid composition is produced with a yield of at least 30% and wherein the composition comprises triglycerides in a concentration of below 5% (w/w).

2. The process of claim 1, wherein the therapeutic concentrated phospholipid composition is produced with a yield between 30%-60%.

3. The process of claim 1, wherein the total phospholipids in the composition are at a concentration of at least 50% (w/w (phospholipids/composition)).

4. The process of claim 1, wherein the composition comprises free and bound docosahexaenoic acid (DHA) and eicosapentaenoic acid (EPA), wherein the total free and bound EPA in the composition is at a concentration of between 15% and 25% (w/w), and the total free and bound DHA in the composition is at a concentration of between 10% and 15% (w/w).

5. The process of claim 1, wherein said therapeutic concentrated phospholipid composition comprises compounds of the Formula I:

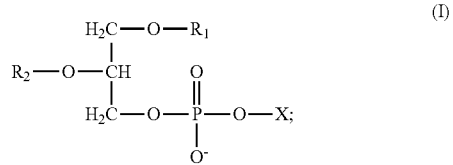

(I)

wherein R1 and R2 each independently optionally represent a docosahexaenoic acid (DHA) or an eicosapentaenoic acid (EPA) residue; and wherein each X is independently selected from —$CH_2CH_2NH_3$, —$CH_2CH_2N(CH_3)_3$ and

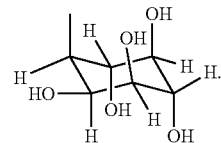

6. The process of claim 1, wherein the RKO comprises at least 15% of FFA.

7. The process of claim 1, wherein the RKO is fractioned by countercurrent supercritical $CO_2$ extraction.

8. The process of claim 1, further comprising the steps of:
   d) separating the fraction concentrated in phospholipids made in step (c) of claim 1 into a first low density layer and a first higher density layer enriched in phospholipids relative to the low density layer;
   e) separating the first higher density layer made in step (d) from the first low density layer;
   f) mixing the first separated higher density layer with an organic solvent comprising at least 85% by weight of a C3-C8 ketone solvent to form a mixture;
   g) fractionating the mixture into a second low density layer and a second higher density layer enriched in phospholipids relative to the first higher density layer; and
   h) separating the second higher density layer enriched in phospholipids from the second low density layer to obtain the concentrated phospholipid composition.

9. The process of claim 8, wherein the concentrated phospholipid composition is mixed with one or more free fatty acids.

10. The process of claim 8, further comprising combining the second layer enriched in phospholipids with a stabilizing agent, a viscosity-reducing agent, or a combination thereof, to produce a phospholipid-enriched fraction.

11. The process of claim 8, wherein the process comprises mixing the RKO and the organic solvent at a ratio of about 5 to about 15 units of volume organic solvent: kg RKO.

12. The process of claim 11, wherein prior to mixing the RKO and the organic solvent, the process comprises heating the RKO to a temperature from about 20° C. to about 70° C.

13. The process of claim 8, further comprising directing the mixture of RKO with the organic solvent through a filter.

14. The process of claim 8, further comprising directing the mixture of RKO with the organic solvent through a first filter and a second filter.

15. The process of claim 8, further comprising combining the second layer enriched in phospholipids with a viscosity-reducing agent.

16. The process of claim 1, wherein the process is a continuous process.

17. The process of claim 1, wherein the total phospholipids in the composition are at a concentration of 55% (w/w (phospholipids/total composition)).

18. The process of claim 1, wherein the total phospholipids in the composition are at a concentration of 60% (w/w (phospholipids/total composition)).

19. The process of claim 1, wherein said RKO is extracted from frozen krill or krill meal.

* * * * *